(12) United States Patent
Reese

(10) Patent No.: US 7,217,279 B2
(45) Date of Patent: May 15, 2007

(54) SUTURE LOOP ANCHOR

(75) Inventor: Karl S. Reese, West Roxbury, MA (US)

(73) Assignee: Ethicon, Inc., Somerville, NJ (US)

(*) Notice: Subject to any disclaimer, the term of this patent is extended or adjusted under 35 U.S.C. 154(b) by 223 days.

(21) Appl. No.: 10/713,788

(22) Filed: Nov. 14, 2003

(65) Prior Publication Data
US 2005/0107828 A1 May 19, 2005

(51) Int. Cl.
*A61B 17/04* (2006.01)

(52) U.S. Cl. .......................... 606/232; 606/60; 606/72

(58) Field of Classification Search .................. 606/60, 606/65, 72, 73, 75, 232, 53, 54, 63, 67, 68, 606/167, 185, 224, 225
See application file for complete search history.

(56) References Cited

U.S. PATENT DOCUMENTS

| | | | |
|---|---|---|---|
| 5,100,417 A * | 3/1992 | Cerier et al. ................. | 606/139 |
| 5,141,520 A | 8/1992 | Goble | |
| 5,224,946 A | 7/1993 | Hayhurst | |
| 5,522,843 A * | 6/1996 | Zang .......................... | 606/232 |
| 5,527,342 A | 6/1996 | Pietrzak et al. | |
| 5,540,718 A | 7/1996 | Bartlett | |
| 5,733,307 A * | 3/1998 | Dinsdale ...................... | 606/232 |
| 5,948,000 A * | 9/1999 | Larsen et al. ................ | 606/232 |
| 5,957,924 A * | 9/1999 | Tormala et al. ............... | 606/72 |
| 5,980,558 A | 11/1999 | Wiley | |
| 6,143,017 A | 11/2000 | Thal | |
| 6,146,407 A | 11/2000 | Krebs | |
| 6,165,203 A | 12/2000 | Krebs | |
| 2002/0120274 A1 | 8/2002 | Overaker | |
| 2002/0161401 A1* | 10/2002 | Steiner ......................... | 606/232 |
| 2002/0161404 A1 | 10/2002 | Steiner | |
| 2003/0088252 A1* | 5/2003 | Kaikkonen et al. ............ | 606/76 |

FOREIGN PATENT DOCUMENTS

DE 0 336 100 A2 2/1989

* cited by examiner

*Primary Examiner*—Michael J. Hayes
*Assistant Examiner*—Michael G. Mendoza
(74) *Attorney, Agent, or Firm*—Emil Richard Skula

(57) ABSTRACT

A suture anchor is provided having a body with at least one suture-receiving channel that extends distally from a proximal end of the body. The suture-receiving channel can include a cavity formed in a distal-most end of the body, or it can terminate at a transversely-extending bore formed through the body. The suture anchor can also include a suture loop that is positioned within the suture-receiving channel and cavity or bore, and that includes a proximal portion that extends proximal of the proximal end of the body.

30 Claims, 5 Drawing Sheets

SUTURE LOOP ANCHOR

FIELD OF THE INVENTION

The present invention relates to suture anchors, and in particular to a suture anchor having a suture loop for receiving an operative suture.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone. The tissue may be attached to the bone during open surgery, or during closed (e.g., arthroscopic) surgical procedures. While many conventional suture anchors are successful in anchoring tissue to bone, they suffer from some disadvantages as well. For example, many conventional suture anchors provide small passageways through which the suture must be threaded, causing difficulties or delays in threading the suture. Moreover, attachment of the suture thread to the anchor, typically at the distal end of the anchor, can result in disadvantageous movement or twisting of the suture thread. Where two free ends of suture thread are required or desired, unwanted tangling and knotting may occur when two suture ends exit the anchor through a single hole in the anchor body or on the same side of the anchor body. Other disadvantages can result where the anchor is a screw-type anchor. For example, the suture thread can be abraded or otherwise damaged when the anchor is threaded into bone. Further, once the anchor is implanted, slidable movement of the suture thread is often prevented.

Accordingly, there remains a need for an improved system for anchoring soft tissue to bone.

SUMMARY OF THE INVENTION

The present invention generally provides a suture anchor system for anchoring tissue to bone that includes an elongate body having proximal and distal ends with a longitudinal axis extending therebetween. In one embodiment, the body includes at least one longitudinally extending bone-engaging surface feature formed thereon, and a continuous suture-receiving channel or recess extends distally from opposed sides of the proximal end of the body around the distal end of the body. The suture-receiving channel is adapted to seat a suture therein, preferably flush or sub-flush with an outer surface of the body. In an exemplary embodiment, the suture-receiving channel is adapted to seat and engage the suture loop, yet allow sliding movement of the suture loop. In another embodiment, the suture-receiving channel can include a substantially concave cavity that is formed in a distal-most end thereof. The cavity can be adapted to seat a knot formed in the suture loop, and more preferably it can be adapted to seat the knot flush or sub-flush with an outer surface of the body. In an exemplary embodiment, the cavity has a substantially spherical shape. The system also preferably includes a first loop of suture thread freely-slidably disposed around the elongate body within the at least one suture-receiving channel. A proximal portion of the loop is positioned proximal to the proximal end of the body.

In yet another embodiment of the present invention, a suture anchor that is adapted to be disposed within bone is provided. The anchor includes an elongate body having a proximal end, a distal end, and at least one discrete bone-engaging surface feature formed thereon and adapted to engage bone. First and second opposed suture-receiving channels are formed in the body and they extending distally from the proximal end of the body. The anchor also includes a transversely-extending suture tunnel formed proximal to the distal end of the body such that the distal end of the body has a substantially solid, cavity-free distal tip. The opposed suture-receiving channels preferably terminate at the suture tunnel and/or they are in communication with the suture tunnel. A suture loop can be disposed within the first and second opposed suture-receiving channels and the transversely-extending suture tunnel, and the suture loop can include a proximal portion positioned proximal of the proximal end of the body. The suture loop can also optionally include a knot that is positioned in the transversely-extending suture tunnel.

A method for anchoring suture in bone is also provided using a suture anchor having a generally elongate body with proximal and distal ends, a suture-receiving member formed on at least a portion of the body, and a suture loop extending around at least a portion of the body and positioned in the suture-receiving member such that a proximal portion of the suture loop is positioned proximal of the proximal end of the elongate body. The method includes the steps of providing an operative suture, forming a bone cavity within a bony structure, passing the operative suture through the proximal portion of the suture loop, and implanting the suture anchor in the bone cavity such that the operative suture extends from the cavity and is freely slidable with respect to the suture loop.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention generally provides a suture anchor that includes a body having proximal and distal ends with at least one suture-receiving channel that extends distally from the proximal end of the body. The suture-receiving channel can include a cavity formed in a distal-most end of the body, or it can terminate at a transversely-extending bore formed through the body. The suture anchor can also include a suture loop that is positioned within the suture-receiving channel and cavity or bore, and that includes a proximal portion that extends proximal of the proximal end of the body. In use, an operative suture can be passed through the proximal portion of the suture loop to attach the operative suture to the anchor. This is particularly advantageous in that the operative loop is freely-slidable with respect to the suture loop, thus facilitating attachment and/or positioning of the operative loop with respect to tissue being anchored to the bone containing the anchor. The use of a suture loop is also particularly advantageous in that it provides a secure attachment of the suture to the anchor, even if fractures or minor breakage occurs to the anchor body during insertion into bone.

Figure 1:
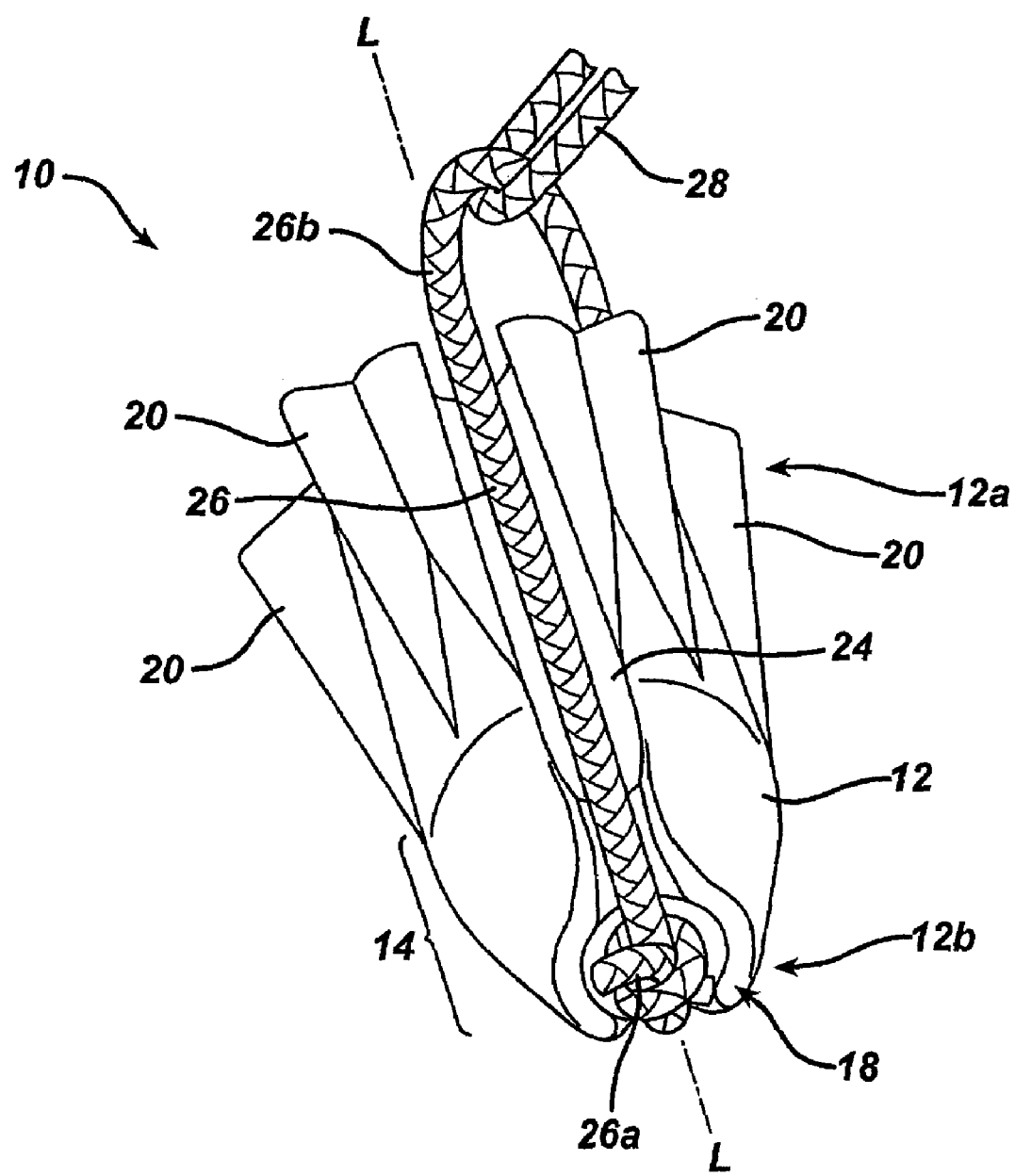
FIG. 1 is distal-side perspective view of one embodiment of a suture anchor in accordance with the present invention.
Figure 2:
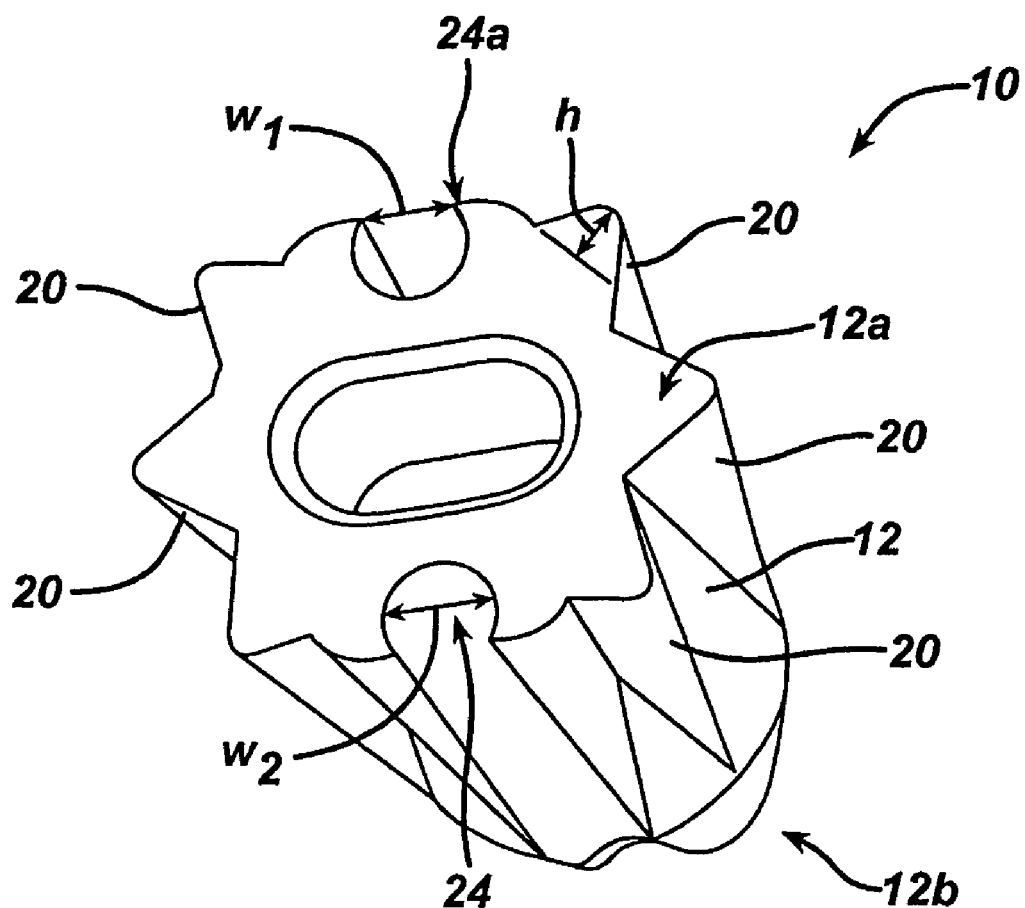
FIG. 2 is a proximal-side perspective view of the suture anchor shown in FIG. 1.

FIGS. 1 and 2 illustrate one embodiment of a suture anchor 10 in accordance with the present invention. As shown, the suture anchor 10 includes a body 12 having proximal and distal ends 12a, 12b with a longitudinal axis L extending therebetween. The body 12 is preferably substantially solid and it can have a bullet-like shape such that the body 12 has a substantially cylindrical proximal portion and it includes a distal tip portion 14 that tapers in a distal direction. The proximal end 12a of the body 12 can have a variety of shapes, but it is preferably substantially planar and includes a driver-receiving element 16 (FIG. 2), such as a blind bore, formed therein for receiving a driver tool that is effective to drive the anchor 10 into bone. The driver-receiving element 16 can have virtually any shape and size, and it is not intended to be limited to a bore. The distal end 12b of the body 12 can also have a shape and size that varies, but preferably the distal end 12b includes a cavity 18 formed therein, as will be discussed in more detail below. In an alternative embodiment, not shown, the distal end 12b can include a pointed and/or sharpened distal tip to facilitate insertion of the anchor 10 into bone.

The body 12 can also include at least one, and preferably several, bone-engaging surface features 20 formed on an outer surface thereof. The surface features 20 are adapted to engage bone to prevent removal of the suture anchor 10 once the anchor 10 is implanted. While the surface features 20 can vary in size and shape, in an exemplary embodiment the surface features 20 are in the form of longitudinally extending ridges, as shown, that extend from a position just proximal to the distal tip 12b and that terminate at the proximal end 12a. Each ridge 20 preferably has a substantially triangular cross-section, shown in FIG. 2, with a height h that increases in a distal-to-proximal direction.

The suture anchor 10 further includes at least one suture-receiving member formed thereon or therein for seating a suture. As shown in FIGS. 1 and 2, the suture-receiving member is in the form of a continuous channel 24 that extends from opposed sides of the proximal end 12a of the body 12 and around the distal tip 12b. The shape and size of the suture-receiving channel 24 can vary, but it is preferably adapted to seat a suture thread 26, as shown in FIG. 1. The channel 24 also preferably has a size and depth that is effective to seat the suture 26 flush or sub-flush with an outer surface of the body 12. This will prevent the suture 26 from being engaged between the anchor 10 and bone when the anchor 10 is implanted. Moreover, such a channel design will prevent damage to the suture 26 during insertion. In an exemplary embodiment, the suture-receiving channel 24 is adapted to engage the suture thread 26, while still allowing sliding movement of the suture thread 26 with respect to anchor 10. Engagement of the suture 26 can be achieved by forming the channel 24 from a partially spherical cutout having an opening 24a (FIG. 2) formed therein that has a width $w_1$ that is smaller than a width $w_2$ of the channel 24. This will allow the opening 24a to retain the suture 26 within the channel 24, while allowing the suture 26 to slide freely within the channel 24. A person skilled in the art will appreciate that the channel 24 can have a variety of other configurations, shapes, and sizes, and that while a generally open channel 24 is shown, the channel 24 can optionally be closed such that the channel 24 is in the form of a generally longitudinally-extending bore formed in the anchor 10.

The channel 24 can also optionally include a cavity 18 formed in the distal-most end 12b of the body 12, as shown in FIG. 1. The cavity 18, which can disrupt the continuous channel 24, or which can optionally be separated from the channel 24 such that the body 12 includes two separate channels, is preferably configured to seat a knot 26a in a suture loop 26 to prevent interference by the knot 26a during insertion of the anchor 10 into bone. Accordingly, the cavity 18 preferably has a substantially hemi-spherical concave shape. In an exemplary embodiment, the cavity 18 is adapted to seat the knot 26a flush or sub-flush with an outer surface of the body 12.

The suture 26 that is disposed within the suture-receiving channel 24 is preferably in the form of a suture loop. As previously stated, the loop 26 can include a knot 26a, or alternatively the loop 26 can be formed from a thread having ends that are otherwise attached to one another through a bonding technique. The suture loop 26 can also optionally be bonded or otherwise attached to the anchor. The loop 26 should, however, have a size that allows a proximal portion 26b of the loop 26 to extend proximally from the proximal end 12a of the body 12. This allows the proximal portion 26b of the loop 26 to form an attachment mechanism for an operative suture thread 28 to be attached to the bone anchor 10. The loop 26 also advantageously allows the operative suture 28 to slide with respect to the loop 26, thus facilitating attachment of tissue to bone.

Figure 3:
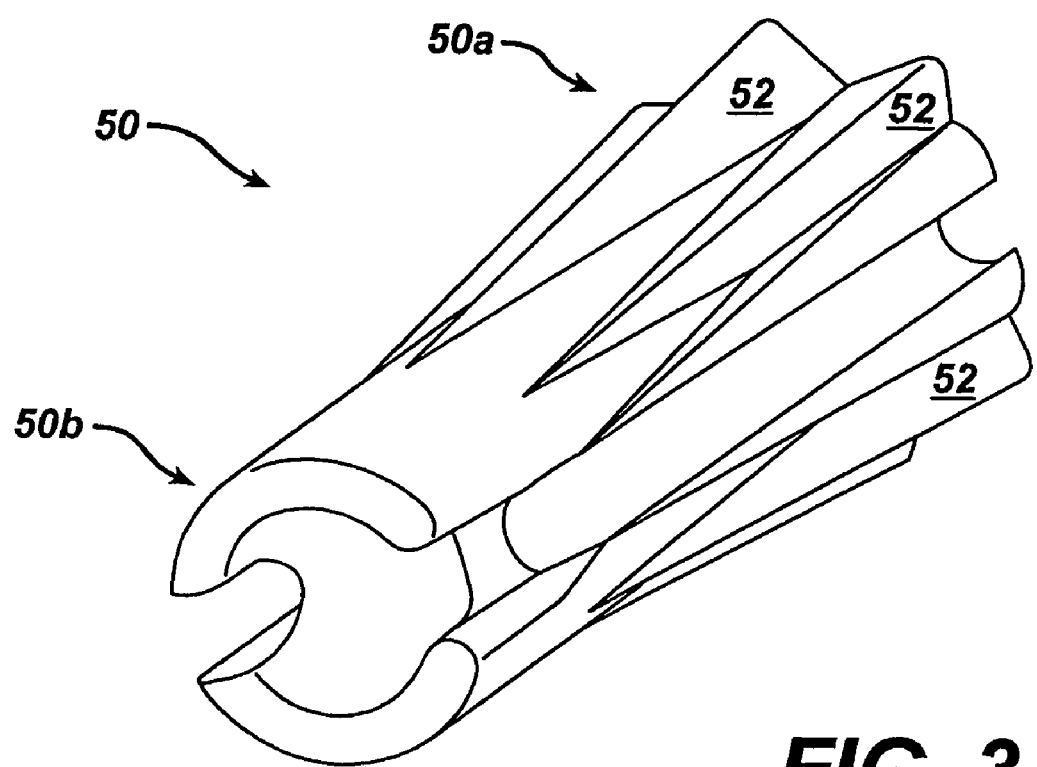
FIG. 3 is a side perspective view of yet another embodiment of a suture anchor in accordance with the present invention.

A person skilled in the art will appreciate that the body 12 of the bone anchor 10 can have a variety of shapes, sizes, and configurations. By way of non-limiting example, FIG. 3 illustrates an anchor 50 that is similar to anchor 10, but that is not bullet-shaped. Rather, as shown, the anchor 50 is substantially cylindrical and includes a flattened proximal end 50a and a non-tapered distal tip 50b. Several bone-engaging surface features 52 are formed thereon and they extend from a substantial mid-portion of the anchor 50 toward the proximal end 50a of the anchor 50 such that the overall circumference of the anchor 50 increases in a distal-to-proximal direction.

Figure 4:
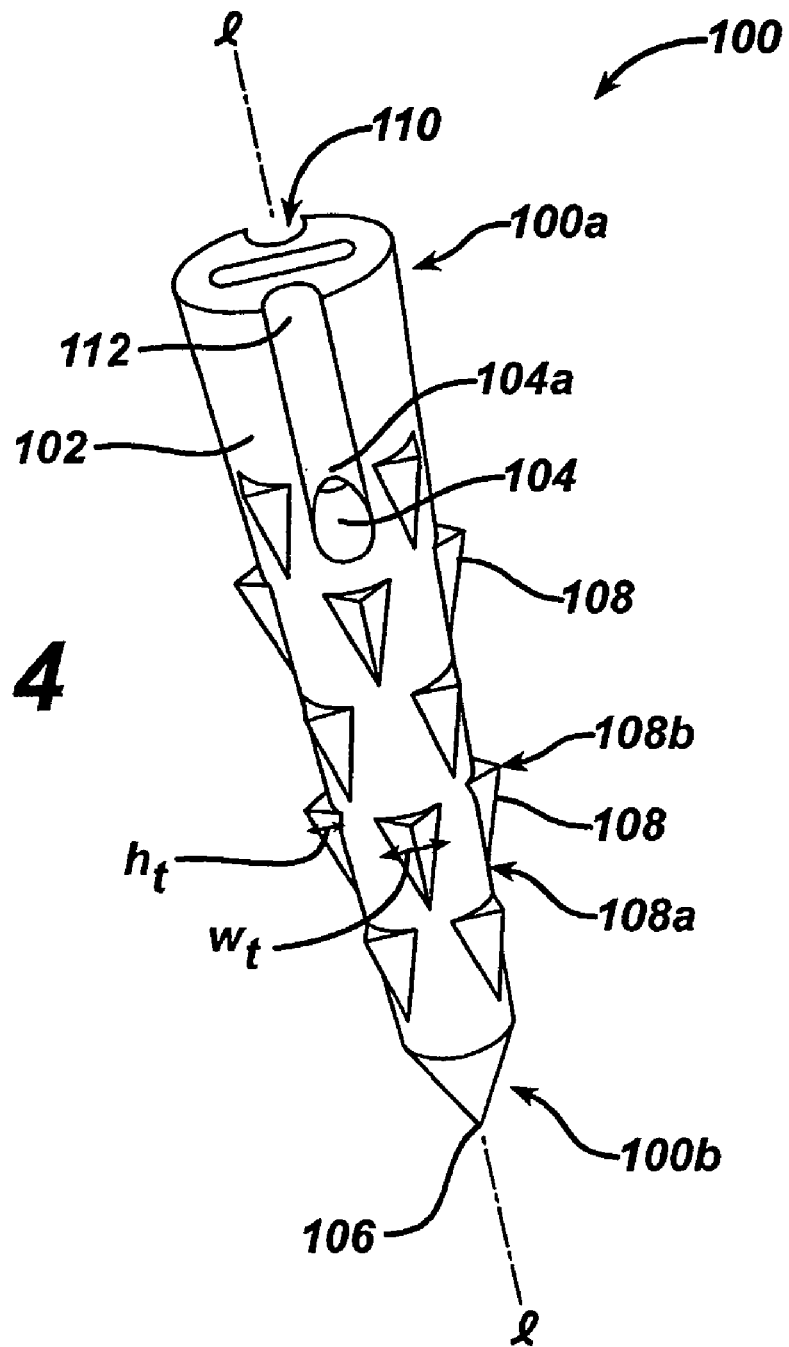
FIG. 4 is a side perspective view of a suture anchor in accordance with yet another embodiment of the present invention.

In another embodiment of the present invention, shown in FIG. 4, the bone anchor 100 can include opposed channels (only one channel 112 is shown) that communicate with a bore 104 for receiving a suture loop (not shown). The bone anchor 100 is similar to bone anchor 10 described above with respect to FIGS. 1–2, and it includes a body 102 that has a generally cylindrical shape and that tapers from a proximal end 100a to a distal end 100b. The distal tip 106 of the body 102 is preferably pointed to facilitate insertion of the body 102 into bone.

The anchor 100 can also include at least one, and preferably several, bone-engaging surface features 108 formed thereon, preferably in the form of several discrete bone-engaging teeth. The shape, size, and location of the teeth 108 can vary, but in an exemplary embodiment the teeth 108 are substantially triangular or pyramidal in shape. The teeth 108 are also preferably longitudinally oriented to facilitate insertion of the anchor 100 into bone. In particular, as shown, the teeth 108 increase in width $w_t$ and height $h_t$ from a distally positioned leading end 108a to a proximally positioned trailing end 108b. A person skilled in the art will appreciate that the suture anchor 100 can include a variety of other bone-engaging surface features formed thereon, including ridges as previously described with respect to FIGS. 1–2.

Continuing to refer to FIG. 4, the suture anchor 100 also preferably includes a suture-receiving member formed thereon for seating a suture loop. The suture-receiving member can have a variety of configurations, but in an exemplary embodiment it is in the form of opposed suture-receiving channels 110, 112, similar to suture-receiving channel 24 described above with respect to FIGS. 1–2. The channels 110, 112 preferably extend distally from the proximal end 100a of the body 102, and they can terminate at a bore 104 that is formed through the body 102 of the anchor 100 at a location that is proximal to the distal end 100b of the body 102, and more preferably at a location that is proximal to a substantial midpoint of the body 102. The bore 104 is preferably a transversely-extending bore, but it can have any shape and size and it can be positioned anywhere on the body 102. The bore 104 should not, however, interfere with the structural integrity of the anchor 100. The bore 104 also preferably has rounded outer edges, e.g., edge 104a, to allow free slidable movement of a suture extending therethrough without causing damage to the suture. By way of non-limiting example, in other embodiments the bore 104 can extend at an angle with respect to a longitudinal axis l of the anchor 100, and/or it can extend along or axially outward from the longitudinal axis l of the anchor 100. A person skilled in the art will appreciate that the bore 104 can have virtually any configuration.

As described above with respect to FIGS. 1–2, bone anchor 100 can also include a suture loop (not shown) coupled thereto. The suture loop can be positioned within the channels 110, 112 and it can extend through the bore 104. A proximal portion of the suture loop should extend proximally of the proximal end 100a of the bone anchor 100 to allow an operative suture to be passed therethrough and coupled to the anchor. In an exemplary embodiment, where the suture loop includes a knot formed therein, the knot is preferably positioned within the bore 104 to prevent interference by the knot during insertion of the anchor 100 into bone.

Figure 5:
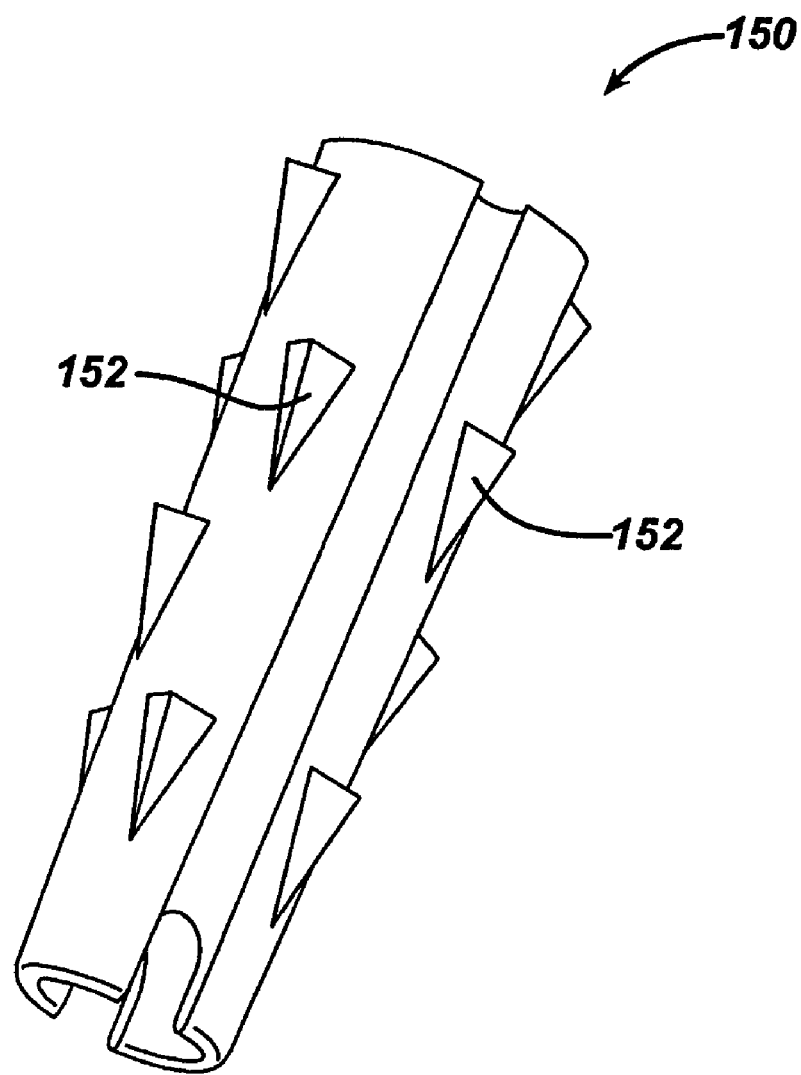
FIG. 5 is a side perspective view of yet another embodiment of a suture anchor according to the present invention.

A person skilled in the art will appreciate that the bone anchors of the present invention can include any combination of features described herein, as well as other features known in the art. By way of non-limiting example, FIG. 5 illustrates another embodiment of a suture anchor 150 having teeth 152 similar to teeth 108, yet the anchor 150 has a substantially cylindrical, elongate shape, and it can include channels (only one channel 154 is shown) that extend along the entire length of the body.

The suture anchor of the present invention can be used for a variety of medical procedures. In an exemplary embodiment, the suture anchor is used in the context of an arthroscopic shoulder repair, and more specifically, for attaching a detached labrum (as might result from a Bankart lesion or rotator cuff tear) to the glenoid rim of a scapula. It will be understood, however, that the methods and devices described herein are equally applicable to connecting detached tissue in other contexts as well. Further, the method described is merely exemplary of the steps involved in using any of the embodiments of the anchors of the present invention.

With reference to FIG. 1 for convenience, the procedure, following medically acceptable patient preparation and anesthetization, generally requires a delivery guide (not shown), e.g., a hollow guide tube, to be positioned at a desired implant site in the vicinity of a joint. A tap, or more preferably, an awl or a punch, is then inserted through the tube and rotated until the depth mark reaches the cortical surface of the patient's bone. A length of suture (e.g., the operative suture 28) is then threaded through the proximal portion 26b of the suture loop 26 on the suture anchor 10, and the remaining portion of the operative suture 28 can be passed through a driver tool. While virtually any driver tool can be used, a typical driver tool includes an elongate shaft having a proximal, handle portion and a distal end having a shape that is configured to fit within the socket or blind bore 16 formed in the proximal end 12a of the suture anchor 10. The driver tool can also preferably include features formed thereon or thereon to receive the operative suture 28 that is coupled to the suture loop 26 on the anchor 10.

Prior to insertion of the anchor 10 into bone, the free ends (not shown) of the operative suture 28 extending proximally from the driver tool can optionally be pulled to hold the suture anchor 10 on the distal end of the driver tool. The anchor 10 can then be inserted into bone by removing the tap from the delivery guide and introducing the driver tool with the anchor 10 attached thereto through the delivery guide. A force can be applied to the driver tool to insert the anchor 10 into the bone tunnel. The driver tool can then be removed, thereby exposing the suture anchor 10 and the sutures 28 extending therefrom. The surgeon can then approximate the free end of detached labrum to the surface of the bone adjacent to the suture anchor 10, and the operative suture 28 can then be threaded through detached labrum and tied to secure the detached labrum to the bone.

The suture anchors of the present invention can be formed from a variety of materials, and can be formed from separate parts which are mated to one another. Preferably, however, the suture anchor is formed as a single unit from a material that is suitable for human implantation, such as metal or plastic, and that is somewhat resilient. Exemplary materials include, for example, metals, metal alloys, absorbable polymers, such as, but not limited to, polylactic acid, polyglycolic acid, and blends and copolymers thereof, non-absorbable polymers, such as, but not limited to, polyethylene, polypropylene, polyurethane, and acetal, and bioceramic materials, such as blends of polymers containing tricalcium phosphate, calcium sulfate, calcium carbonates, and hydroxy appetite.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor system for anchoring tissue to bone, comprising:

a substantially solid, elongate body having proximal and distal ends with a longitudinal axis extending therebetween, the body including at least one longitudinally extending bone-engaging surface feature formed thereon and extending substantially between the proximal and distal ends;

a continuous suture-receiving channel extending distally from opposed sides of the proximal end of the body around the distal end of the body, the suture-receiving channel being adapted to seat a suture therein;

a first loop of suture thread freely-slidably disposed around the elongate body within the at least one suture-receiving channel, the suture loop including a proximal portion that is positioned proximal to the proximal end of the body.

2. The suture anchor of claim 1, wherein the suture-receiving channel is adapted to seat the suture loop flush or sub-flush with an outer surface of the body.

3. The suture anchor of claim 1, wherein the substantially solid, elongate body includes a plurality of longitudinally extending bone-engaging surface features formed thereon.

4. The suture anchor of claim 1, wherein the suture-receiving channel is adapted to seat and engage the suture loop, yet allow slidable movement of the suture loop.

5. The suture anchor of claim 1, wherein the suture-receiving channel includes a substantially concave cavity formed in a distal-most end of the body, the cavity being adapted to seat a knot formed in the suture loop.

6. The suture anchor of claim 5, wherein the cavity is adapted to seat the knot flush or sub-flush with an outer surface of the body.

7. The suture anchor of claim 5, wherein the cavity has a substantially hemi-spherical shape.

8. The suture anchor of claim 1, wherein the at least one longitudinally extending bone-engaging surface feature comprises at least one ridge.

9. The suture anchor of claim 1, wherein the at least one longitudinally extending bone-engaging surface feature comprises at least one discrete pyramid-shaped surface feature.

10. The suture anchor of claim 1, wherein the elongate body is substantially cylindrical and includes a distal tip portion that tapers in a distal direction.

11. The suture anchor of claim 1, further comprising a driver-receiving element formed in the proximal end of the elongate body.

12. A suture anchor adapted to be disposed within bone, comprising:
an elongate body having a proximal end, a distal end, and at least one discrete longitudinally extending bone-engaging surface feature formed thereon extending substantially between the proximal and distal ends and adapted to engage bone;
a transversely-extending suture tunnel formed proximal to the distal end of the body such that the distal end of the body has a substantially solid distal tip;
first and second opposed suture-receiving channels formed in the body and extending from the proximal end of the body and terminating at the suture tunnel; and
a suture loop disposed within the first and second opposed suture-receiving channels and the transversely-extending suture tunnel, the suture loop including a proximal portion positioned proximal of the proximal end of the body.

13. The suture anchor of claim 12, wherein the first and second opposed suture-receiving channels are in communication with the suture tunnel.

14. The suture anchor of claim 12, wherein the elongate body includes a plurality of discrete bone-engaging surface features formed thereon and adapted to engage bone.

15. The suture anchor of claim 12, wherein the suture loop includes a knot that is positioned within the transversely-extending suture tunnel.

16. The suture anchor of claim 12, wherein the first and second opposed suture-receiving channels are adapted to seat the suture loop flush or sub-flush with an outer surface of the body.

17. The suture anchor of claim 12, wherein the first and second opposed suture-receiving channels are adapted to seat and engage the suture loop, yet allow slidable movement of the suture loop.

18. The suture anchor of claim 17, wherein the at least one discrete bone-engaging surface feature comprises at least one discrete pyramid-shaped surface feature.

19. The suture anchor of claim 12, wherein the elongate body tapers from a proximal end to a distal end.

20. The suture anchor of claim 12, further comprising a driver-receiving element formed in the proximal end of the elongate body.

21. A method for anchoring suture in bone, comprising:
providing a suture anchor having
a generally elongate body with proximal and distal ends,
a suture-receiving member formed on at least a portion of the body, and
a suture loop extending around at least a portion of the body and positioned in the suture-receiving member such that a proximal portion of the suture loop is positioned proximal of the proximal end of the elongate body;
providing an operative suture;
forming a bone cavity within a bony structure;
passing the operative suture through the proximal portion of the suture loop; and
implanting the suture anchor in the bone cavity such that the operative suture extends from the cavity and is freely slidable with respect to the suture loop.

22. The method of claim 21, wherein the suture-receiving member comprises opposed longitudinally oriented suture-receiving channels formed in an outer surface of the body and originating at and extending distally from the proximal end of the body.

23. The method of claim 22, wherein the suture-receiving member further includes a cavity formed in a distal-most end of the elongate body and adapted to seat a knot formed in the suture loop.

24. The method of claim 22, wherein the suture-receiving member further includes a transversely-extending suture tunnel formed distal to the proximal end, the opposed suture-receiving channels terminating at the suture tunnel, and the suture loop extending through the suture tunnel.

25. The method of claim 22, wherein the suture-receiving channels are adapted to seat the suture loop flush or sub-flush with an outer surface of the body.

26. The method of claim 22, wherein the suture-receiving channels are adapted to seat and engage the suture loop, yet allow slidable movement of the suture loop.

27. The method of claim 21, wherein the suture-receiving member comprises a single suture-receiving channel formed in an outer surface of the body and extending distally from opposed sides of the proximal end of the body around the distal end of the body.

28. The method of claim 21, wherein the at least one bone-engaging surface feature comprises longitudinally extending ridges.

29. The method of claim 21, wherein the elongate body tapers from a proximal end to a distal end.

30. A suture anchor adapted to be disposed within bone, comprising:
an elongate body having a proximal end, a distal end, and at least one discrete longitudinally extending bone-engaging surface feature formed thereon extending substantially between the proximal and distal ends and adapted to engage bone;
a transversely-extending suture tunnel formed proximal to the distal end of the body such that the distal end of the body has a substantially solid distal tip,
first and second opposed suture-receiving channels formed in the body and extending from the proximal end of the body and terminating at the suture tunnel; and
a suture loop disposed within the first and second opposed suture-receiving channels and the transversely-extending suture tunnel, the suture loop including a proximal portion positioned proximal of the proximal end of the body, wherein the suture loop includes a knot that is positioned within the transversely-extending suture tunnel.

* * * * *